US005417875A

United States Patent [19]

Nozaki

[11] Patent Number: 5,417,875

[45] Date of Patent: May 23, 1995

[54] CONTAINING N-ACYLAMINO ACID SALT AND GERMICIDE

[75] Inventor: Toshio Nozaki, Chiba, Japan

[73] Assignee: Kao Corporation, Tokyo, Japan

[21] Appl. No.: 985,196

[22] Filed: Dec. 3, 1992

[30] Foreign Application Priority Data

Dec. 4, 1991 [JP] Japan .................................. 3-320695

[51] Int. Cl.[6] .......................... C11D 1/10; C11D 3/24; C11D 3/48; A61K 7/50

[52] U.S. Cl. .................................... 252/106; 252/107; 252/117; 252/173; 252/546; 252/DIG. 5; 252/DIG. 7; 252/DIG. 13

[58] Field of Search ................. 252/106, 107, DIG. 5, 252/DIG. 14, 546, 117, 527

[56] References Cited

U.S. PATENT DOCUMENTS

| | | | |
|---|---|---|---|
| 2,846,398 | 8/1958 | Beaver | 252/106 |
| 3,660,296 | 5/1972 | Lavril | 252/106 |
| 3,707,505 | 12/1972 | Maeda | 252/136 |
| 3,725,547 | 4/1973 | Kooistra | 252/106 |
| 3,950,277 | 4/1976 | Stewart | 252/541 |
| 4,111,844 | 9/1978 | Polony | 252/106 |
| 4,118,332 | 10/1978 | Apostolatos | 252/107 |
| 4,919,846 | 4/1990 | Nakama | 252/542 |
| 5,190,747 | 3/1993 | Sekiguchi | 424/56 |

FOREIGN PATENT DOCUMENTS 0415598 3/1991 European Pat. Off. ............ 252/546

*Primary Examiner*—Dennis Albrecht
*Attorney, Agent, or Firm*—Sughrue, Mion, Zinn, Macpeak & Seas

[57] ABSTRACT

A detergent composition is disclosed, which comprises the components (A) and (B):

(A) a secondary amide type N-acylamino acid salt represented by formula (1):

$$R^1CONH(CH_2)_nCOOM^1 \qquad (1)$$

wherein $R^1CO$ represents a straight chain acyl group having 10 to 16 carbon atoms;

n is an integer of 1 or 2; and $M^1$ represents a sodium or potassium atom or an alkanolammonium group when n is 1, or a potassium atom or an alkanolammonium group when n is 2; and (B) a germicide selected from the group consisting of triclosan, trichlorocarbanilide, isopropylmethylphenol and chlorhexidine hydrochloride. This detergent composition shows a high detergency, gives a good feel upon use, causes little irritation to skin and causes little damage to hair. Further, it exerts a good germicidal effect which can last for a prolonged period of time. It is particularly suitable for cleansing the skin.

9 Claims, No Drawings

CONTAINING N-ACYLAMINO ACID SALT AND GERMICIDE

FIELD OF THE INVENTION

This invention relates to a detergent composition. More particularly, it relates to a detergent composition which causes little irritation to skin, causes little damage to hair, has a high detergency, gives a good feel upon use and exerts an intense germicidal effect lasting for a prolonged period of time.

BACKGROUND OF THE INVENTION

Conventional germicidal detergents have employed medical detergent compositions containing various surfactants together with germicides. When a germicide is added to a detergent, however, the germicide is washed away from the skin or the hair together with the detergent so that it does not fully remain on the skin or the hair. As a result, such a germicide is hardly effective on bacteria adhering to the skin or the hair after cleansing. In order to cope with this problem, the content of the germicide may be increased so as to elevate its germicidal effect. However, it is feared that this measure might induce skin irritation or allergic reactions. Although the germicidal effect is tentatively elevated thereby, it still does not last for a sufficiently long period of time.

Accordingly, an objective of the present invention is to provide a detergent Composition which causes little irritation to skin, causes little damage to hair and exerts an excellent germicidal effect lasting for a prolonged period of time.

Under these circumstances, the present inventors have conducted extensive investigations. As a result, they have successfully found that a detergent composition, which has a high detergency, causes little irritation to skin, causes little damage to hair, gives a good feel upon use and exerts an excellent germicidal effect lasting for a prolonged period of time, can be obtained by using a germicide together with an N-acylamino acid salt of a specific structure, thus completing the present invention.

SUMMARY OF THE INVENTION

Accordingly, the present invention provides a detergent composition which comprises the components (A) and (B):

(A) an N-acylamino acid salt represented by formula (1):

$$R^1CONH(CH_2)_nCOOM^1 \quad (1)$$

wherein $R^1CO$ represents a straight chain acyl group having 10 to 16 carbon atoms;

n is an integer of 1 or 2; and $M^1$ represents a s odium or potassium atom or an alkanolammonium group when n is 1, or a potassium atom or an alkanolammonium group when n is 2; and (B) a germicide selected from the group consisting of triclosan, trichlorocarbanilide, isopropylmethylphenol and chlorhexidine hydrochloride.

DETAILED DESCRIPTION OF THE INVENTION

The N-acylamino acid salt employed in the present invention as the component (A) reacts with calcium contained in, for example, tap water and forms plate crystals showing a high lubricating property. Thus, a detergent composition containing the N-acylamino acid salt gives a good feel upon use and a high smoothness after cleansing. The lubricating property of the plate crystals formed by the reaction between the N-acylamino acid salt and calcium may be determined by, for example, measuring the cc efficient of static friction of these plate crystals on lyophilized porcine skin (Alloask, trade name, manufactured by Kotai Kasei Kogyo K.K.) regenerated with isotonic sodium chloride solution. Crystals showing a lower coefficient of static friction throughout regeneration and drying, than the untreated one, are referred to as highly lubricant.

In the present invention, the N-acylamino acid salt forms plate crystals that incorporate therein the germicide. Thus the crystals adhering to, for example, the skin are scarcely washed away. As a result, the germicide can exert its germicidal effect which can last for a long time, even when used in a small amount.

In the above-mentioned formula (1) of the N-acylamino acid salt, the straight-chain acyl group represented by $R^1CO$ has 10 to 16, preferably, 12 to 14 carbon atoms. Preferred examples thereof include caprinoyl, lauroyl and myristoyl groups and, among them, lauroyl and myristoyl groups are more preferred. When the number of carbon atoms in the $R^1CO$ group exceeds 16, the lubricating property of the resulting plate crystals tends to be deteriorated. When the number of carbon atoms is less than 10, on the other hand, the foaming property of the detergent composition tends to be deteriorated.

$M^1$ in the above formula (1) is sodium or potassium atom or an alkanolammonium group when n is 1, or potassium atom or an alkanolammonium group when n is 2. Examples of the alkanolammonium group represented by $M^1$ in the above formula (1) include cations of monoethanolamine, diethanolamine and triethanolamine, with the cation of triethanolamine being preferred. Among them, potassium atom is preferred as $M^1$.

It is very important in the present invention that the above-mentioned N-acylamino acid salt has a secondary amide type structure wherein the N-acyl group is such a straight chain acyl group as defined above. When the acyl group constituting the N-acyl group is branched or the N-acylamino acid salt has a tertiary amide type structure, the formation of the plate crystals is suppressed or the crystals formed have a poor lubricating property and may exhibit stickiness, which makes it difficult to live a preferable feel. Further, an N-acylamino acid salt of formula (1) wherein n is 2 and $M^1$ is a sodium salt has a high Krafft point and poor solubility in water. Thus such an N-acylamino acid salt cannot be preferably employed in liquid detergent compositions.

The germicide to be used in the present invention as the component (B) is one or more compounds selected from the following (1) to (4).

(1) Triclosan represented by the following formula:

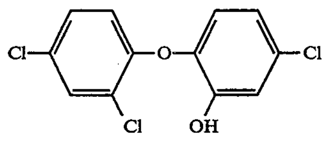

(2) Trichlorocarbanilide (TCC) represented by the following formula:

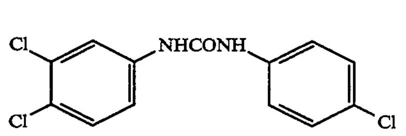

(3) Isopropylmethylphenol (4) Chlorhexidine hydrochloride

Either one of the above-mentioned germicides or a mixture thereof may be used.

In the detergent composition according to the present invention, the content of the component (A) generally ranges from 5 to 95% by weight based on the total weight of the composition but it may vary depending on the formulation of the detergent composition. For example, a liquid detergent may preferably contain from 5 to 50% by weight of the component (A), a pasty detergent may preferably contain from 15 to 70% by weight of the component (A), while a solid detergent may preferably contain from 40 to 95% by weight of the component (A). On the other hand, the content of the component (B) in the detergent composition of the present invention may range from 0.01 to 5.0% by weight, preferably from 0.05 to 2.0% by weight, in any formulations of the detergent composition.

The detergent Composition according to the present invention may further contain a higher fatty acid salt as a component (C) so as to give a detergent excellent in foaming properties and foam texture, in addition to the above-mentioned characteristics. Examples of the higher fatty acid salt (C) include, for example, base salts of fatty acids having 8 to 22 carbon atoms. Specific examples thereof include base salts of single fatty acids (for example, lauric acid, myristic acid, palmitic acid, isostearic acid, oleic acid) or mixed fatty acids (for example, coconut oil fatty acid, beef tallow fatty acid). Examples of the base include inorganic bases such as sodium and potassium and ammonium; alkanolamines such as monoethanolamine, diethanolamine, triethanolamine, 2-amino-2-methylpropanol and 2-amino-2-methylpropanediol; and basic amino acids such as lysine and arginine. It is not always necessary that these higher fatty acid salts (C) are added in the form of fatty acid salts. Namely, the fatty acid and the base may be separately added so as to form the fatty acid salt in the formulation system. Either one of these higher fatty acid salts or a mixture thereof may be used. The content of the higher fatty acid salt (C) in the detergent composition according to the present invention may vary depending on the content of the component (A). That is to say, the weight ratio of (C)/(A) may range from 1/20 to ½, preferably from 1/10 to ⅓.

The detergent composition of the present invention may further contain surfactants arbitrarily selected from, for example, artionic surfactants such as alkyl sulfuric acid salts, alkyl sulfonic acid salts, polyoxyethylene alkyl sulfuric acid salts, alkyl benzenesulfonic acid salts, N-acylsarcosine salts, N-acyl-N-methyltaurine salts, N-acylmethyl-β-alanine salts, α-olefinsulfonic acid salts, higher fatty acid ester sulfonic acid salts, alkyl ether acetic acid salts, polyoxyethylene alkyl ether acetic acid salts, amidoamino acid salts (for example, sodium 2-alkyl-N-hydroxyethylimidazolinium betains), polyoxyethylene alkylsulfosuccinic acid salts, N-acylsarcosine salts and acylglutamic acid salts; nonionic surfactants such as fatty acid amides, polyoxyethylene alkyl ethers, sugar esters, sugar ethers and sugar amides; and amphoteric surfactants such as imidazoline surfactants and betaine surfactants, so long as the effects of the present invention are not deteriorated thereby. Among these additional surfactants, alkylsulfuric acid salts, polyoxyethylene alkyl ether sulfuric acid salts, amidoamino acid salts, N-acylmethyltaurine salts, polyoxyethylene alkylsulfosuccinic acid salts, N-acylmethyl-β-alanine salts, N-acylsarcosine salt and an acylglutamic acid salts are preferred and polyoxyethylene alkyl ether sulfuric acid salts and amidoamino acid salts are more preferred.

The detergent composition of the present invention may further contain other components commonly used in the field of detergents, so long as the effects of the present invention are not deteriorated thereby. Examples of such components include humectants such as propylene glycol, sorbitol and glycerol; viscosity controllers Such as carboxyvinyl polymer, methyl cellulose, ethanol and polyoxyethylene glycol distearate; pearlizing agents; perfumes; colorants; UV absorbers; anti-oxidants; anti-inflammatory agents and preservatives.

The detergent composition of the present invention may be produced by conventional methods and formulated into, for example, a paste, a gel, a solution or a solid. The detergent composition of the present invention is useful for cleansing the skin or shampooing the hair, in particular, it is suitable for cleansing the skin.

To further illustrate the present invention in greater detail, the following Examples are given. However it should be understood that the present invention is not restricted thereto.

EXAMPLE 1

Detergents of Compositions specified in Table 1 below were prepared. Then the adsorbed amount of the germicide remaining after washing was determined with respect to each detergent composition in the following manner.

A lyophilized porcine skin (Alloask, trade name, manufactured by Kotai Kasei Kogyo K.K.) having a size of 15 mm×15 mm was regenerated with isotonic sodium chloride solution and immersed into 100 ml of a 20-fold-dilute sample detergent solution for 30 seconds. Then the porcine skin was removed from the solution and thoroughly rinsed in 1-l of water of 20° DH. Next, the porcine skin was immersed into ethanol to extract the remaining germicide (triclosan) and the amount of the germicide thus extracted was determined based on the absorbance at 280 nm measured by means of an UV-absorbing meter.

The results are shown in Table 1. In the table, Product No. 1 is according to the present invention, while Product No. 2 is comparison.

TABLE 1

| Composition (% by weight) | Product No. 1 | 2 |
|---|---|---|
| Lauroyl-$\beta$-alanine TEA | 30 | — |
| Coconut oil fatty acid TEA | — | 30 |
| Triclosan | 0.5 | 0.5 |
| Purified water | balance | balance |
| Adsorbed residual amount ($\mu g/cm^2$) | 2.344 | 1.857 |

EXAMPLE 2

Detergent compositions specified in Table 2 were prepared. An expert panel was asked to wash his or her hands with the detergents and evaluate the foaming property and the feel upon use of the detergents in accordance with the following criteria.

Foaming:

A: Excellent foaming

B: Good foaming

C: Poor foaming

Feel upon use:

A: Good foam breakage and smooth touch

B: Bad foam breakage and slimy touch

C: Intense Squeaky touch without smooth nor slimy touch

The results are shown in Table 2. In the table, Product Nos. 1–5 are according to the present invention, while Product Nos. 6 and 7 are comparison.

TABLE 2

| Component (% by weight) | Product No. 1 | 2 | 3 | 4 | 5 | 6 | 7 |
|---|---|---|---|---|---|---|---|
| Lauroyl-$\beta$-alanine K salt | 20 | 20 | 20 | 20 | 20 | — | — |
| Lauroylamidopropyl-dimethylcarboxybetaine | — | — | — | — | 3 | — | — |
| Lauroyl-N-methyl-$\beta$-alanine Na salt | — | — | — | — | — | 20 | — |
| Coconut oil fatty acid TEA | — | — | — | — | — | — | 30 |
| Lauric acid K salt | — | — | — | 2 | 2 | — | — |
| Triclosan | 0.5 | — | — | 0.5 | 0.5 | 0.5 | 0.5 |
| Isopropylmethylphenol | — | 0.5 | — | — | — | — | — |
| Chlorhexidine Hydrochloride | — | — | 0.1 | — | — | — | — |
| Purified water | balance | balance | balance | balance | balance | balance | balance |
| Evaluation | | | | | | | |
| Foaming | B | B | B | A | A | B | A |
| Feel upon use | A | A | A | A | A | B | C |

Note: "TEA" means triethanolamine.

EXAMPLE 3

Composition:

| Component | Amount (% by weight) |
|---|---|
| (1) Lauroyl-$\beta$-alanine triethanolamine | 25 |
| (2) Triclosan | 0.4 |
| (3) Triethanolamine laurate | 4 |
| (4) Triethanolamine myristate | 2 |
| (5) Perfume | 0.5 |
| (6) Dibutylhydroxytoluene | 0.2 |
| (7) Ethanol | 3 |
| (8) Purified water | balance |

The components (1) to (4) were dissolved in heated water (8) and cooled. Then the components (5) to (7) were added thereto to give a liquid detergent composition. when used for cleansing the body, the liquid detergent composition thus obtained exerted a superior deodorant effect due to its high germicidal effect, was excellent in foaming and foam breakage and gave a good feel upon use while exhibiting a high smoothness throughout rinsing and after drying.

EXAMPLE 4

Composition:

| Component | Amount (% by weight) |
|---|---|
| (1) Lauroyl-$\beta$-alanine K salt | 10 |
| (2) Trichlorocarbanilide | 0.1 |
| (3) Lauric acid K salt | 1 |
| (4) Myristic acid K salt | 0.5 |
| (5) Perfume | 0.5 |
| (6) Dibutylhydroxytoluene | 0.3 |
| (7) Ethanol | 4 |
| (8) Purified water | balance |

The components (1) to (4) were dissolved in heated water (8) and cooled. Then the components (5) to (7) were added thereto to give a liquid detergent composition.

When used for cleansing the body, the liquid detergent composition thus obtained exerted a superior deodorant effect due to its high germicidal action, was excellent in foaming and foam breakage and gave a good feel upon use while exhibiting a high smoothness throughout rinsing and after drying.

The detergent composition according to the present invention shows a high detergency, gives a good feel upon use, causes little irritation to skin and causes little damage to hair. Further, it exerts a good germicidal effect which can last for a prolonged period of time. It is particularly suitable for cleansing the skin.

While the invention has been described in detail and with reference to specific embodiments thereof, it will be apparent to one skilled in the art that various changes and modifications can be made therein without departing from the spirit and scope thereof.

What is claimed is:

1. A detergent composition which comprises the components (A) and (B):

(A) an N-acylamino acid salt represented by formula (1):

$$R^1CONH(CH_2)_nCOOM^1 \quad (1)$$

wherein $R^1CO$ represents a straight chain acyl group having 10 to 16 carbon atoms;

n is an integer of 1 or 2; and $M^1$ represents a sodium or potassium atom or an alkanolammonium group when n is 1, or a potassium atom or an alkanolammonium group when n is 2; and (B) triclosan, wherein said component (A) is present in an amount of from 5 to 95% by weight and said Component (B) is present in an amount of from 0.05 to 2.0% by weight.

2. A detergent composition of claim 1, which further contains the following component (C):

(C) a higher fatty acid salt selected from the group consisting of inorganic bases, alkanolamines and basic amino acids, wherein the weight ratio of component (C) to component (A) is 1/20 to ½.

3. A detergent composition of claim 2, wherein said inorganic base is sodium, potassium or ammonium; said alkanolamine is monoethanolamine, diethanolamine, triethanolamine, 2-amino-2-methylpropanol or 2-amino-2-methylpropanediol; and said basic amino acid is lysine or arginine.

4. A detergent composition of claim 1, wherein said $M^1$ in said formula (1) is potassium atom.

5. A detergent composition of claim 1, wherein said $R^1CO$ in said formula (1) is lauroyl group or myristoyl group.

6. A detergent composition of claim 1, wherein n in formula (1) is 2.

7. A liquid detergent composition which comprises the components (A) and (B):

(A) from 5 to 50% by weight of an N-acylamino acid salt represented by formula (1):

$$R^1COHH(CH_2)_nCOOM^1 \quad (1)$$

wherein $R^1CO$ represents a straight chain acyl group having 10 to 16 carbon atoms;

n is an integer of 1 or 2; and $M^1$ represents a sodium or potassium atom or an alkanolammonium group when n is 1, or a potassium atom or an alkanolammonium group when n is 2; and (B) from 0.05 to 2.0% by weight of triclosan.

8. A liquid detergent composition which comprises the components (A) and (B):

(A) from 5 to 50% by weight of an N-acylamino acid salt represented by formula (1):

$$R^1COHN(CH_2)_nCOOM^1 \quad (1)$$

wherein $R^1CO$ represents a straight chain acyl group having 10 to 16 carbon atoms;

n is 2; and $M^1$ represents a potassium atom or an alkanolammonium group; and (B) from 0.05 to 2.0% by weight of triclosan.

9. A solid detergent composition which comprises the components (A) and (B):

(A) from 40 to 95% by weight of an N-acylamino acid salt represented by formula (1):

$$R^1COHN(CH_2)_nCOOM^1 \quad (1)$$

wherein $R^1CO$ represents a straight chain acyl group having 10 to 16 carbon atoms;

n is an integer of 1 or 2; and $M^1$ represents a sodium or potassium atom or an alkanolammonium group when n is 1, or a potassium atom or an alkanolammoninm group when n is 2; and (B) from 0.05 to 2.0% by weight of triclosan.

* * * * *